United States Patent

Davis et al.

[11] Patent Number: 5,833,666
[45] Date of Patent: Nov. 10, 1998

[54] CATHETER FIXATION ASSEMBLY

[75] Inventors: Charles R. Davis, Hanover Park; David Schucart, Homewood; Lev Melinyshyn, Buffalo Grove, all of Ill.

[73] Assignee: Uresil Corporation, Skokie, Ill.

[21] Appl. No.: 532,236

[22] Filed: Sep. 22, 1995

Related U.S. Application Data

[63] Continuation-in-part of Ser. No. 279,834, Jul. 25, 1995, abandoned, which is a continuation of Ser. No. 157,672, Nov. 23, 1993, abandoned.

[51] Int. Cl.⁶ .................................................. A61M 25/02
[52] U.S. Cl. ................................. 601/180; 128/DIG. 26
[58] Field of Search ................................... 604/174, 179, 604/180; 128/DIG. 26

[56] References Cited

U.S. PATENT DOCUMENTS

| | | | |
|---|---|---|---|
| 3,487,837 | 1/1970 | Peterson | 604/180 |
| 3,683,911 | 8/1972 | McCormick | 64/180 |
| 4,275,721 | 6/1981 | Olson | 128/DIG. 26 |
| 4,360,025 | 11/1982 | Edwards | 604/180 |
| 4,392,853 | 7/1983 | Muto | 604/180 |
| 4,579,120 | 4/1986 | MacGregor | 604/174 |
| 4,645,492 | 2/1987 | Weeks | 604/180 |
| 4,755,173 | 7/1988 | Konopka et al. | 604/180 |
| 4,856,504 | 8/1989 | Yamamoto et al. | 604/180 |
| 4,874,380 | 10/1989 | Hesketh | 128/DIG. 26 |
| 4,915,694 | 4/1990 | Yamamoto et al. | 604/186 |
| 4,986,815 | 1/1991 | Schneider | 604/180 |
| 5,069,206 | 12/1991 | Croshie | 604/174 |
| 5,215,531 | 6/1993 | Maxson et al. | 128/DIG. 26 |

*Primary Examiner*—Paul J. Hirsch
*Attorney, Agent, or Firm*—Laff, Whitesel, Conte & Saret, Ltd.

[57] ABSTRACT

An assembly for externally securing a catheter at or adjacent to an exit site on a body tissue which includes a resilient member and a detachably removable and adjustable clamp which allow for a gentle bend in the catheter so that kinking is prevented.

17 Claims, 3 Drawing Sheets

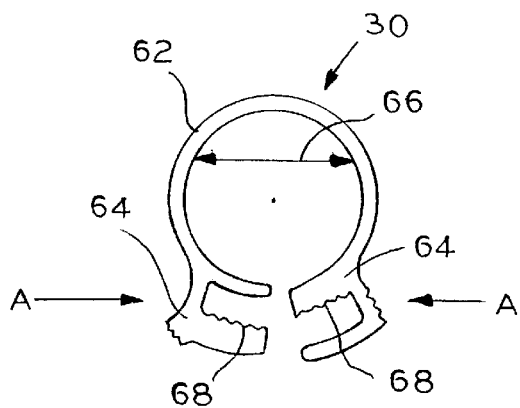
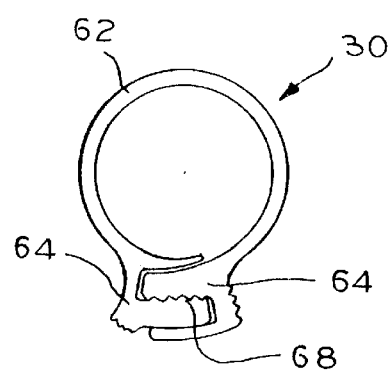
FIG.6                    FIG.7
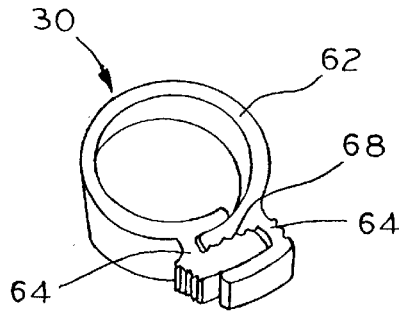
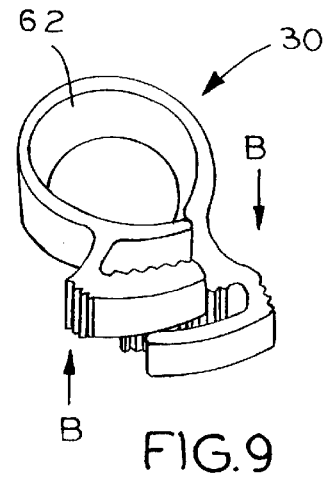
FIG.8                    FIG.9
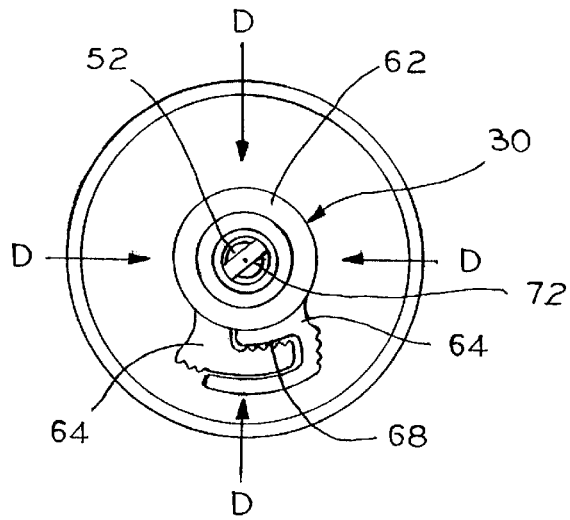
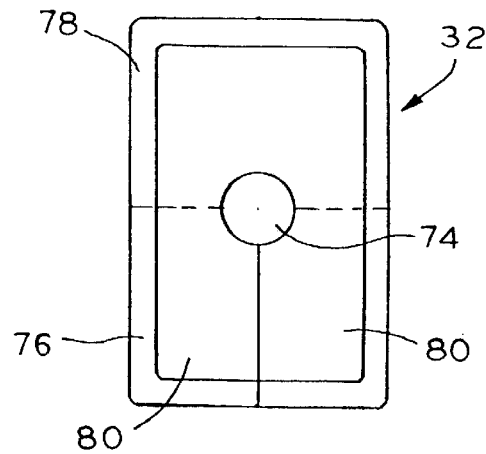
FIG.10                   FIG.11

CATHETER FIXATION ASSEMBLY

This application is a continuation-in-part of U.S. Ser. No. 08/279,834 filed Jul. 25, 1994, which is a continuation of U.S. Ser. No. 08/157,672 filed Nov. 24, 1993, now abandoned.

FIELD OF THE INVENTION

This invention relates generally to catheters. More particularly, this invention relates to an assembly for externally securing a catheter at or adjacent to an exit site on a body tissue.

BACKGROUND OF THE INVENTION

It is a common practice to catheterize human medical patients for various diagnostic and therapeutic reasons. For example, accident victims often require catheterization by the paramedic in an emergency vehicle or by a medical technician or doctor in an operating room or special procedures setting. Catheterization is accomplished by the insertion of a generally tubular catheter into a site for permitting the injection or withdrawal of fluids or other materials.

Although the catheterization of patients is a critical and necessary part of many medical procedures, there are certain disadvantages associated with the use of catheters, including the risk of introducing potentially life-threatening infections. Such infections are commonly seen in patients wherein the catheters have been introduced into body areas subject to movement on breathing, such as the thorax and the abdomen. Such breathing movement causes the air-exposed and often contaminated catheter to move into and out of the patient's body tissue potentially permitting infection to enter.

Another related problem is the premature or inadvertent removal of catheters from the body tissue. Premature or inadvertent catheter removal is caused by, for example, the entanglement of the patient's hands or feet or an article of clothing with the catheter. Such premature catheter removal can cause damage to internal structures, interruption of the procedure and the need for catheter reinstallation.

Yet another problem with catheter use is the tendency of catheters to kink and close off, especially in that portion of the catheter adjacent the drainage site. Kinking interferes with the withdrawal and injection of fluids through the catheter. Catheter fixation devices have been introduced in an effort to eliminate or decrease the above-described problems. One such known catheter fixation device is a generally flat, rectangular device which includes a flexible grooved channel for holding a size 8 through 14 French catheter parallel to the cuff. A cable or pull tie is loosely placed within a slot beneath the cuff groove for securing the catheter to the cuff. The cable or pull tie must be irreversibly cut for catheter removal. The cuff which includes an adhesive backing, is positioned adjacent the drainage site causing the catheter to bend and form an acute angle as it exits the drainage site.

Another known catheter fixation device is a generally cylindrical disc which orients a catheter parallel to the body tissue and which further includes a radially extending grooved channel for bending the catheter prior to its exit from the site. The bent catheter forms an acute angle as it exits the site. The grooved channel terminates at one end at the apex of a V-shaped opening in the center of the disc. Moreover, the grooved channel accommodates catheters of varying diameters. A pull tie loosely and irreversibly secures the catheter to the disc which, in turn, is secured to the body tissue by an adhesive or other suitable fastening means, such as a suture.

Yet another known catheter fixation device is a cylindrical disc which includes a centrally located collar for orienting a catheter parallel to the body tissue while circumferentially and perpendicularly securing the catheter to the exit site. A pull tie loosely and nonuniformly circumscribes the collar for irreversibly squeezing the collar against the catheter to secure the catheter to the disc. An adhesive or other fastening means is used to secure the disc to the body tissue. The cylindrical disc is adapted to fit all catheter sizes.

While the above prior art catheter fixation devices may, in some instances, prevent short-term kinking in catheters or temporarily eliminate in and out movement and resulting infection at catheter drainage sites, they are often inadequate for prolonged use for reasons set forth below.

First, kink prevention is especially difficult in fixation devices that require that the catheter bend or twist at the point of insertion into the body tissue. This is because the bent portions of the catheters are more susceptible to kinking than are the straight portions of the catheters, especially during bodily movement of the patient.

Second, the known fixation devices include cables or pull ties for orienting and securing the catheters within the devices. These ties are inadequate for several reasons. The first reason is that the ties fail to adequately secure the catheters. This is due, in part, to the fact that the ties cannot uniformly apply pressure around the catheters.

Third, the ties of known fixation devices are irreversibly tightened during use and must be cut for removal. The irreversible nature of the ties makes it extremely difficult, if not impossible, to adjust the tightness of the tie for adequately securing the catheter to the fixation device. Thus, if the tie is too loose, the catheter is prone to sliding movement or inadvertent removal from the body tissue; if the tie is too tight, the catheter is subject to kinking and/or closing off problems.

Fourth, the known catheter fixation devices are typically adapted to accommodate a wide range of catheter diameters so that a single fixation device may be used to secure several differently sized catheters. While this feature may maximize the utility of a single catheter fixation device, it has the disadvantage of providing a poor fit for catheters with smaller diameters which contributes to the problems associated with catheter slippage and premature removal from the body tissue.

Despite the numerous disadvantages with the above catheter fixation devices, they are still widely used. Thus, while these catheter fixation devices may have some limited effectiveness in preventing kinking and closing off of catheters, they do so in a less than satisfactory manner.

Accordingly, an object of the present invention is to provide a catheter fixation assembly that securely fixes the catheter to the body tissue.

It is another object of the present invention to provide a catheter fixation assembly that orients and secures the catheter parallel to the body tissue without kinking and closing off the catheter.

It is another object of the present invention to provide a catheter fixation assembly which precludes the catheter from moving in and out of the body tissue as the patient breathes or otherwise moves.

It is another object of the present invention to provide a catheter fixation assembly which eliminates the premature or accidental removal of the catheter from the body tissue.

It is another object of the present invention to provide a catheter fixation assembly that minimizes infection at the drainage and exit site.

It is another object of the present invention to provide a catheter fixation assembly which is convenient to use.

It is another object of the present invention to provide a catheter fixation assembly that is custom fit to the catheter.

Other objects and advantages of the invention will appear hereinafter.

SUMMARY OF THE INVENTION

The present invention, in a preferred embodiment, accomplishes the foregoing objects by providing a catheter fixation assembly for externally securing a catheter at or adjacent to an exit site on a body tissue that comprises a resilient member, a detachably removable and adjustable clamp, and an adhesive dressing. The resilient member includes either a collar or a radially extending support arm for receiving the catheter. Both the collar and the radially extending support arm allow for a gentle bend in the catheter and thus prevent kinking. The adjustable clamp is mounted on the collar or the radially extending support arm of the resilient member for securing the catheter within the resilient member. The adhesive dressing is used to securely fix the resilient member at or adjacent to the exit site.

The catheter includes an outer diameter which is substantially the same as the inner diameter of the collar and the radially extending support arm of the resilient member for providing the catheter with a custom fit. The catheter is generally oriented in parallel relationship to the body tissue.

The resilient member is individually sized for catheter diameters 6F through 14F. The resilient member may include a plurality of openings for suturing the catheter fixation assembly at or adjacent to the exit site. The sutures may be used with or without the adhesive dressing. The resilient member is preferably made of silicone or urethane.

The adjustable clamp is preferably flexible and includes two laterally movable arms with interlocking teeth for closing and locking the clamp and for securing the catheter within the resilient member. The closed clamp may be unlocked and opened for removing the catheter by laterally displacing the interlocked arms. The clamp may be completely closed without affecting the inner-lumen of the catheter and may be repeatedly opened and closed as needed.

The resilient member, adjustable clamp, and adhesive dressing preferably are packaged together in a sterile envelope to form a ready-to-use catheter fixation kit for convenience and ease of use. The kit may also include a catheter.

Thus, the invention provides a catheter fixation assembly for externally securing a catheter at or adjacent to an exit site on a body tissue. The inventive assembly eliminates the inconvenience and potential problems of suturing, kinking and closing off of catheters, pulling out of the catheters, and in and out movement of the catheters with breathing.

The above, as well as other objects and advantages of the invention, will become apparent from the following detailed description of the preferred embodiments, reference being made to the accompanying drawings.

BRIEF DESCRIPTION OF THE DRAWINGS

FIG. 6 is a plan view of the clamp of FIG. 2, illustrating its appearance in an open and unlocked position.

FIG. 7 is a plan view of the clamp of FIG. 6, illustrating its appearance in a closed and locked position.

FIG. 8 is a perspective view of the clamp of FIG. 7.

FIG. 9 is a perspective view of the clamp of FIGS. 7 and 8, illustrating the disengaging of the clamp arms for opening and unlocking the clamp.

FIG. 10 is a plan view of the assembly of FIG. 1.

FIG. 11 is a plan view of the adhesive dressing of FIG. 3.

DETAILED DESCRIPTION OF THE INVENTION

Figure 1:
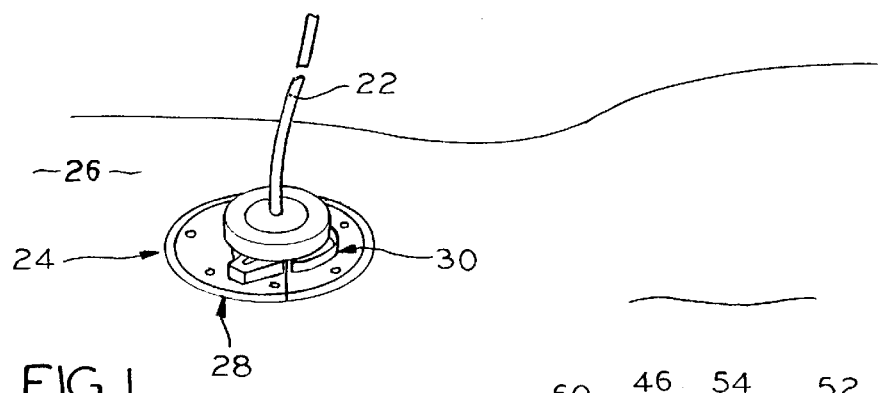
FIG. 1 is a perspective view of the resilient member and adjustable clamp at the exit site.

Generally referring to FIGS. 1–3 and 15, the invention provides an assembly for externally securing a catheter 22 at or adjacent to an exit site 24 on a body tissue 26, comprising a resilient member 28, 28b a detachably removable and adjustable clamp 30, and an adhesive dressing 32. Clamp 30 is mounted on resilient member 28, 28b and secures the catheter within the resilient member at or adjacent to the exit site. Adhesive dressing 32 securely fixes resilient member 28, 28b at or adjacent to the exit site while minimizing the possibility of infection.

Referring to FIGS. 4–5 and 15–16, in a preferred embodiment, resilient member 28, 28b is a generally cylindrical disc 34 having a lower surface 36 and an upper surface 38 which is downwardly tapered toward the lower surface of the disc. A plurality of openings 58 are located on upper surface 38 adjacent the circumference of disc 34 for optionally suturing the disc at or adjacent to the exit site.

Clamp 30 includes a generally cylindrical body portion 62 with two independently and integrally formed arms 64 that are laterally movable, as indicated by arrows A in FIG. 6. Movable arms 64 of clamp 30 each include a plurality of interlocking teeth 68 for closing and locking the clamp (see FIGS. 7 and 8) and for securing the catheter within resilient member 28, 28b (see FIGS. 10 and 15). Likewise, the closed and locked interlocking teeth 68 of movable arms 64 may be disengaged by laterally displacing the interlocked arms 64, as indicated by arrows B in FIG. 9. The disengaged clamp arms 64 form an opening 70 (see FIG. 2) through which the catheter may be inserted into or removed from resilient member 28.

Hemostats (not shown) may be used for closing and opening the clamp.

Figure 3:
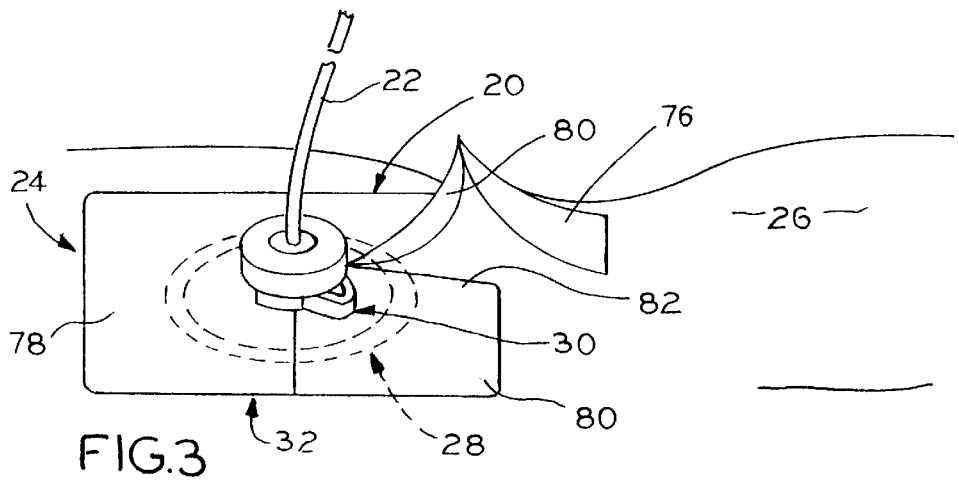
FIG. 3 is a perspective view of the catheter fixation assembly, illustrating its application to a body tissue at the exit site.
Figure 15:
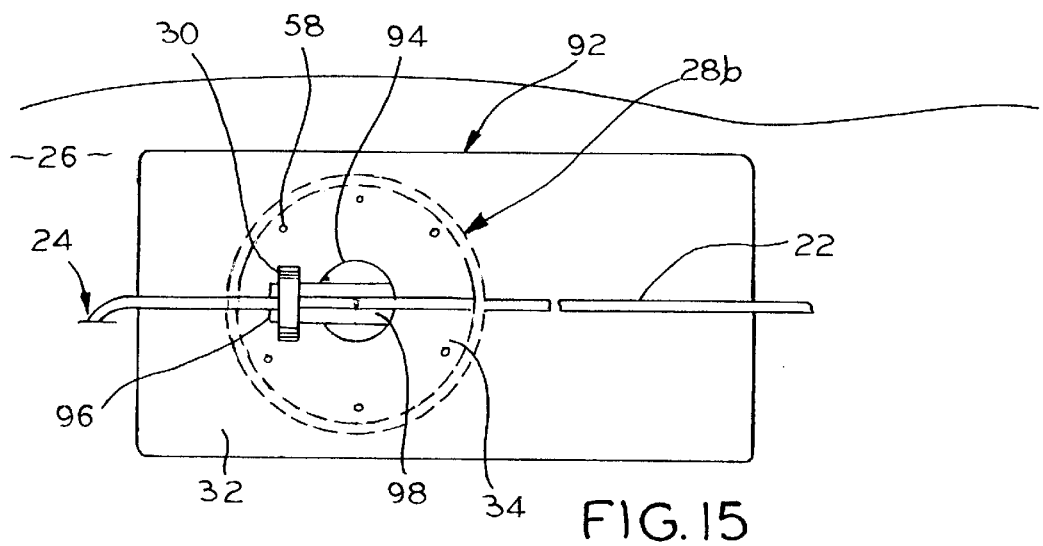
FIG. 15 is a plan view of the catheter fixation assembly adjacent to the exit site.

The catheter assembly is preferably secured at or adjacent to the exit site of the patient by an adhesive dressing 32, as shown in FIGS. 3, 11 and 15. In the preferred embodiment, adhesive dressing 32 includes a centrally located opening 74 and release paper 76 that comprises a large section 78 and two small sections 80, as shown by the perforated lines in FIG. 11.

The catheter fixation assembly may externally secure a catheter either at or adjacent to an exit site on a body tissue. When the catheter fixation assembly is to be secured at an exit site on a body tissue, resilient member 28 which includes a collar 40 is used. Alternatively, when the catheter fixation assembly is to be secured adjacent to an exit site, resilient member 28b with a radially extending support arm 94 (FIG. 15) is used. Both collar 40 and radially extending support arm 94 allow for a gentle bend in the catheter so that kinking is prevented.

Figure 2:
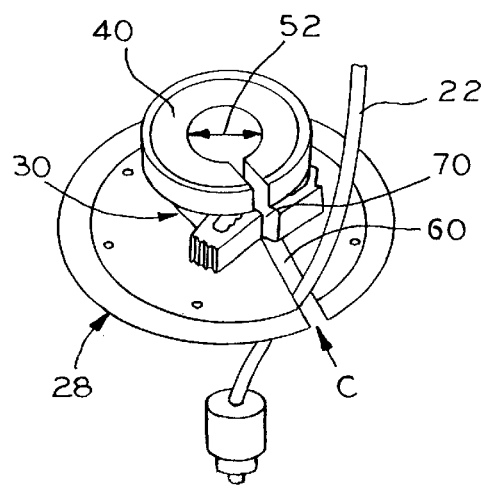
FIG. 2 is a perspective view of the resilient member and detachably adjustable clamp of FIG. 1.
Figure 4:
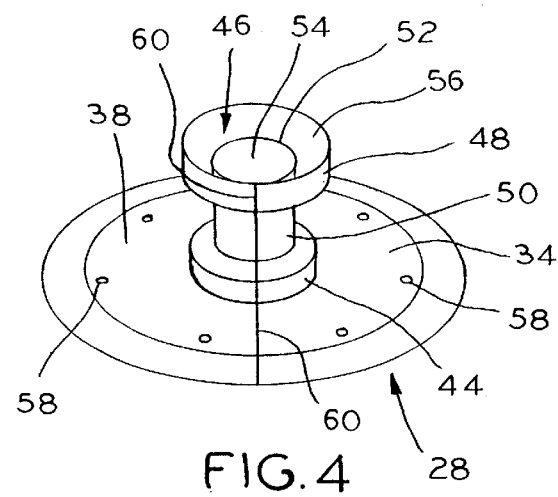
FIG. 4 is a perspective view of the resilient member of FIG. 1, with the adjustable clamp not shown.
Figure 5:
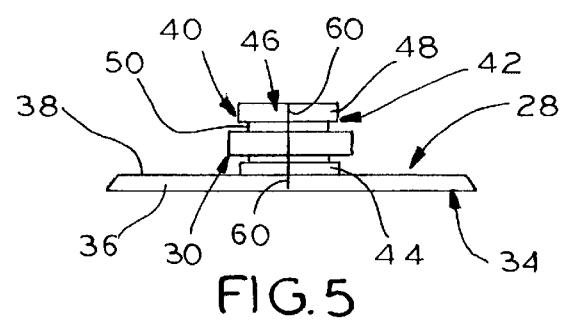
FIG. 5 is a side view of the resilient member and clamp of FIG. 2.

Generally referring to FIGS. 1–3, the catheter fixation assembly used to secure a catheter 22 at an exit site 24 on a body tissue 26 is generally denoted by the numeral 20. As shown in FIGS. 4 and 5, resilient member 28 includes a collar 40 which is integrally formed with and centrally located on upper surface 38 and includes an outer diameter 42 with a bottom portion 44 and a top portion 46 that forms a flange 48. A circumferentially extending groove 50 is located between top portion 46 and bottom portion 44 of collar 40.

Collar 40 further includes an inner diameter 52 that defines an opening 54 through which the catheter passes and is concentrically circumscribed. Inner diameter 52 of collar 40 is substantially the same as outer diameter 72 of the catheter for providing the catheter with a custom fit (see FIG. 10). Thus, a series of resilient members 28 can be specifically and individually sized for catheters having various outer diameters.

The outer edge of flange 48 ramps down to the collar opening 54 in a continuous fashion, thereby creating a concave upper surface 56. It is important that concave surface 56 completely circumscribe collar opening 54 and extend all the way to the edge of flange 48 so that catheter 22 is supported by the entire concave surface and thus gently bends as it exits the collar opening. Accordingly, kinking is prevented.

As shown in FIGS. 5 and 6, clamp 30 is rigidly mounted within groove 50 between bottom portion 44 and top portion 46 of collar 40 and includes an inner diameter 66 with dimensions that substantially correspond to the dimensions of the groove. Flange 48 maintains clamp 30 within groove 50 and prevents it from passing top portion 46 and slipping off collar 40 of the resilient member.

In use, catheter 22 is first introduced into a properly prepared site on the patient's body tissue using standard medical techniques. Next, the introduced catheter is inserted into the individually sized collar opening 54 of resilient member 28 by transversely threading the catheter through radially extending slit 60 of the resilient member and clamp opening 70 of movable arms 64 of the clamp, as shown by the arrow C in FIG. 2. Clamp opening 70 of the movable arms 64 must be aligned with the radially extending slit 60 prior to the insertion of the catheter into collar opening 54 (see FIG. 2).

Subsequent to its insertion into the resilient member, the catheter fixation 5 assembly is positioned directly over a dry and clean exit site on the body tissue so that cylindrical disc 34 contacts the tissue surrounding the site (see FIGS. 1 and 3). Movable arms 64 of clamp 30 are then inwardly and laterally displaced to close and lock teeth 68 (see FIG. 6). The closed and locked clamp causes cylindrical body portion 62 of clamp 30 to uniformly engage and circumferentially press inwardly against collar 40 of the resilient member, as shown by arrows D in FIG. 10. The clamp-induced pressure on collar 40 is, in turn, transmitted to the portion of the catheter in collar opening 54 without affecting the inner lumen of the catheter. Thus, when clamp 30 is closed, its inner diameter is slightly less than the dimensions of both the groove and outer diameter 72 of the catheter and, therefore, securely fixes the catheter within collar opening 54. Moreover, because the catheter includes an outer diameter which is matched to the inner diameter 52 of collar 40, the catheter is provided with a custom fit which cooperates with clamp 30 in securely maintaining the catheter within the collar opening.

To secure the catheter assembly to the exit site, large section 78 of the release paper is removed first and the adhesive dressing is then placed around the catheter so that opening 74 of the dressing circumscribes collar 40 of the resilient member (see FIG. 3). The remaining small sections 80 of release paper 76 are subsequently removed from the dressing with their edges slightly overlapping along an edge 82 for enhanced dressing security. Edge 82 is preferably oriented towards the patient's feet. Likewise, movable arms 64 preferably overlap small sections 80 of the dressing adjacent opening 74 (see FIG. 3).

Tincture of benzoin may be applied to the exit site on the body tissue to further improve the adhesive system.

Removal of the catheter from the resilient member is accomplished by first unlocking and opening the clamp by disengaging teeth 68 with opposing vertical movement (see FIG. 9). Next, the catheter is moved first through clamp opening 70 which is between movable arms 64 of the open clamp and finally through the radially extending slit of the resilient member. Again, clamp opening 70 must be aligned with radially extending slit 60 as the catheter is removed from the resilient member.

Figure 12:
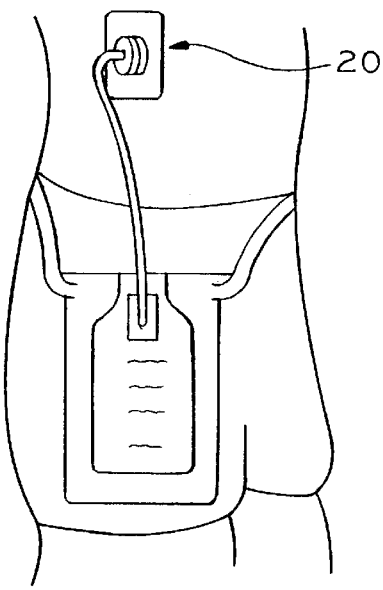
FIG. 12 is a partial perspective view of the assembly of FIG. 3, illustrating its appearance as mounted onto the body tissue of a patient and attached to drainage means.

As shown in FIG. 12, the catheter is oriented in parallel relationship to the patient's body tissue but is perpendicularly secured to and within the collar opening of the resilient member. As previously mentioned, it is the concave upper surface 56 adjacent to and circumscribing the collar opening which enables the catheter to be perpendicularly secured to the resilient member without kinking and which further orients the catheter parallel to the patient's body tissue. Moreover, the large radius of upper surface 56 also prevents kinking in the catheter.

Figure 14:
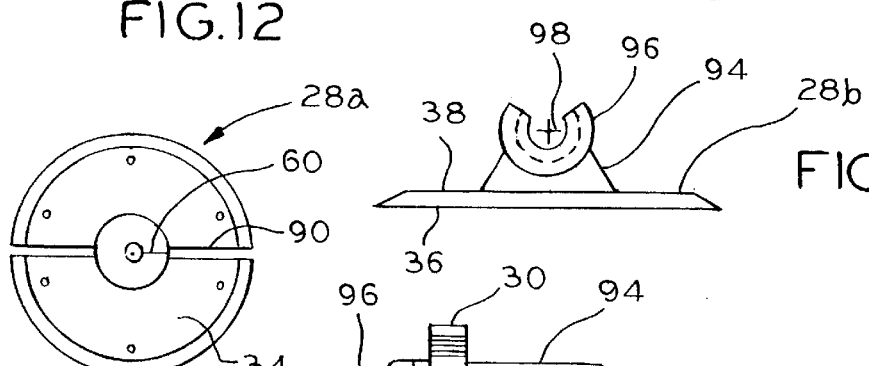
FIG. 14 is a plan view of the resilient member with an open strip across the cylindrical disc.

In an alternative embodiment, resilient member 28a includes open strip 90 which transverses cylindrical disc 34 of the resilient member and is aligned with radially extending slit 60, as shown in FIG. 14. Open strip 90 permits air access to the exit site and thereby enhances the healing process. The open strip also allows oozing fluids to escape so that microbiological growth is minimized. Moreover, open strip 90 facilitates the opening of radially extending slit 60 during the insertion and removal of the catheter to and from the resilient member.

Figure 16:
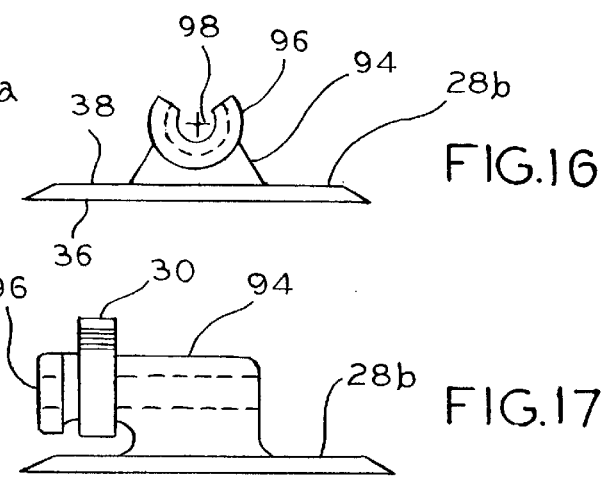
FIG. 16 is a front view of the radially extending support arm.
Figure 17:
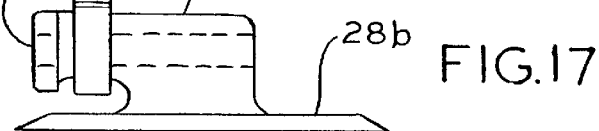
FIG. 17 is a side view of the radially extending support arm and adjustable clamp.

Generally referring to FIG. 15, the catheter fixation assembly used to secure catheter 22 adjacent rather than at an exit site 24 on body tissue 26 is generally denoted by the numeral 92. As shown in FIG. 17, resilient member 28b of this alternative embodiment has a radially extending support arm 94 which is mounted on the resilient member and includes lip 96 which generally circumscribes the distal end of the arm. Support arm 94 includes a longitudinal circular channel 98 which extends through the arm 94 and lip 96, as shown in FIG. 16. The inner diameter of channel 98 in which catheter 22 rests is substantially the same as the outer diameter of the catheter for providing the catheter with a custom fit. Thus, a series of resilient members 28 can be specifically and individually sized for catheters having various outer diameters.

Clamp 30 is rigidly mounted adjacent lip 96 on radially extending support arm 94. The dimensions of clamp inner diameter 66 substantially correspond to the dimensions of support arm 94. Lip 96 prevents clamp 30 from slipping off arm 94 of the resilient member.

In use, catheter 22 is first introduced into a properly prepared site on the patient's body tissue using standard medical techniques. Next, the introduced catheter is inserted into the individually sized longitudinal circular channel 98 of resilient member 28b. The catheter fixation assembly is then positioned adjacent to a dry and clean site on the body tissue. In a preferred embodiment, there is approximately a one to two inch space between resilient member 28b and stoma exit site 24. Movable arms 64 of clamp 30 are then inwardly and laterally displaced to close and lock teeth 68 (see FIG. 6) to secure the catheter within channel 98 of resilient member 28b in the same manner described above with respect to collar 40.

The catheter assembly is secured adjacent to the exit site according to essentially the same procedure described above, except that opening 74 of the dressing circumscribes radially extending support arm 94 of the resilient member, rather than collar 40.

Radially extending support arm 94 of catheter assembly 92 allows for fixation of catheters that exit the patient on an acute angle. Because the catheter runs parallel and is positioned close to the patient's body, it is less likely to become entangled with the patient's hands, feet or clothing. The positioning of the resilient member adjacent to the exit site also facilitates the cleaning of the exit site because it is easier to remove and replace the dressing. In addition, air is permitted to reach the exit site to enhance healing and oozing fluids are allowed to escape from the exit site.

Removal of the catheter from the resilient member is accomplished by first unlocking and opening the clamp by disengaging teeth 68 with opposing vertical movement (see FIG. 9). The catheter can then be removed through clamp opening 70 which is between movable arms 64 of the open clamp and by sliding the catheter out of longitudinal circular channel 98.

Assemblies 20 and 92 may be used in conjunction with any gravity drainage bag (see FIG. 12) or other suitable drainage/collection system. Moreover, assemblies 20 and 92 may optionally be sutured at or adjacent to the exit site.

Figure 13:
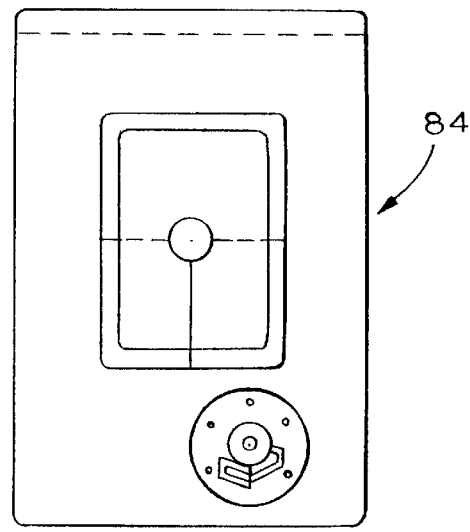
FIG. 13 is a plan view of the assembly of FIG. 3. illustrating its appearance in a packaged kit.

Assemblies 20 and 92 are preferably packaged as a kit 84 (see FIG. 13) that provides a complete system. Kit 84 includes the individually sized resilient member with the detachably removable and adjustable clamp, and the adhesive dressing. Kit 84 is sealed and sterile.

The material from which assemblies 20 and 92 are constructed includes silicone for the resilient member and hard plastic or hard rubber for the clamp. The adhesive dressing may include any thin, flexible material with an adhesive backing. In an alternative embodiment, urethane may be used for further securing the resilient member at or adjacent to the exit site. Assemblies 20 and 92 have not been described in terms of approximate measurements, as it should be understood that the dimensions of the assemblies, including the diameters of the collar opening, the radially extending support arm and the clamp, may vary according to need.

Therefore, it should be recognized that, while the present invention is described above in connection with illustrative embodiments, these embodiments are not intended to be exhaustive or limiting of the invention. Rather, the invention is intended to cover all alternatives, modifications, and equivalents included within its spirit and scope, as defined by the appended claims.

We claim:

1. An assembly for externally securing a catheter at or adjacent to an exit site on a body tissue comprising:

a resilient member having a base for attachment to the body tissue and means for retaining the catheter, said retaining means comprising a resilient, radially extending support arm with an open longitudinal circular channel spaced from the base; and a detachably removable and adjustable clamp for uniformly tightening the catheter within the retaining means.

2. The assembly of claim 1 further comprising an adhesive dressing for securing said resilient member at or adjacent to the exit site.

3. The assembly of claim 1 wherein said adjustable clamp includes two laterally movable arms with interlocking teeth for closing and locking said adjustable clamp and securing the catheter within said resilient member.

4. The assembly of claim 3 wherein said clamp, when closed, may be opened for removing the catheter by laterally displacing the interlocking teeth.

5. The assembly of claim 1 wherein the catheter has an outer diameter which is substantially the same as the inner diameter of said retaining means.

6. The assembly of claim 5 wherein said outer diameter of said catheter is greater than said inner diameter of said retaining means when said assembly is closed.

7. The assembly of claim 1 wherein said resilient member includes a plurality of openings for suturing said resilient member at or adjacent to the exit site.

8. The assembly of claim 1 wherein said resilient member is adjacently positioned about one to two inches from the exit site.

9. A system for externally securing a catheter at or adjacent to an exit site on a body tissue comprising:

a resilient member having retaining means with an inner diameter that is substantially the same as the outer diameter of the catheter; and a detachably removable and adjustable clamp for uniformly tightening the retaining means to grip the catheter without affecting the inner diameter of the catheter, said adjustable clamp having an inner diameter when closed corresponding with the outer diameter of said retaining means, said clamp being reversible to release the grip on the catheter.

10. The system of claim 9 wherein said retaining means is a collar with a channel for concentrically circumscribing the catheter.

11. The system of claim 9 wherein said retaining means is a radially extending support arm with a longitudinal circular channel.

12. The system of claim 9 wherein said adjustable clamp includes two laterally movable arms with interlocking teeth for closing and locking said adjustable clamp and securing the catheter within said resilient member and for opening and releasing the catheter.

13. The system of claim 12 wherein said clamp, when closed, may be unlocked and opened for removing the catheter by laterally displacing the interlocking teeth.

14. An assembly for externally securing a catheter at or adjacent to an exit site on a body tissue comprising:
- a resilient member with an upstanding collar having a channel for receiving and concentrically circumscribing the catheter and a flange encircling the collar at its free end, said collar having a concave upper surface extending to the outer edge of the flange; and
- a detachably removable and adjustable clamp for uniformly tightening the catheter within said channel.

15. An assembly for externally securing a catheter at or adjacent to an exit site on a body tissue comprising:
- a resilient member with means for retaining the catheter; and
- a detachably removable and adjustable locking clamp for gripping the catheter within said retaining means, the clamp having a closed position whereby when the clamp is closed the inner diameter of the catheter is unaffected, and for releasing the catheter therefrom.

16. The assembly of claim 15 wherein said retaining means is a collar with a channel for concentrically circumscribing the catheter.

17. The assembly of claim 15 wherein said retaining means is a radially extending support arm with a longitudinal circular channel.

* * * * *